United States Patent [19]

Mazzio

[11] Patent Number: 5,099,441
[45] Date of Patent: Mar. 24, 1992

[54] METHOD FOR DETERMINING THERMAL CONDUCTIVITY INCORPORATING DIFFERENTIAL SCANNING CALORIMETRY

[75] Inventor: Victor F. Mazzio, Rochester, N.Y.

[73] Assignee: Eastman Kodak Company, Rochester, N.Y.

[21] Appl. No.: 200,288

[22] Filed: May 31, 1988

[51] Int. Cl.⁵ .................... G06F 15/20; G01N 25/18
[52] U.S. Cl. .................... 364/557; 364/556; 374/44; 374/137
[58] Field of Search .............. 364/550, 556, 557; 374/11, 12, 31, 44, 137

[56] References Cited

U.S. PATENT DOCUMENTS

| | | | |
|---|---|---|---|
| 3,319,456 | 5/1967 | Speros et al. | 374/11 |
| 3,733,887 | 5/1973 | Stanley et al. | 374/44 |
| 3,971,246 | 7/1976 | Sumikama et al. | 374/44 |
| 4,155,244 | 5/1979 | Bhattacharyya | 374/44 |
| 4,284,690 | 8/1981 | Koehler et al. | 374/44 |
| 4,368,991 | 11/1983 | Hentze | 374/12 |
| 4,630,938 | 12/1986 | Piorkowska-Palczewska | 374/44 |

OTHER PUBLICATIONS

"Differential Thermal Analysis Apparatus for Temperatures up to 1575° C."; NRL Report 4942; K. G. Skinner, 1957.
Thermochimica Acta, 126 (1988), by H. Liu et al., "Effect of Sample Size and Heating Rate on the DSC Process for Reactions of High Enthalpy", pp 81-92.
Thermochimica Acta, 115 (1987), by T. Boddington and P. G. Laye, "The Measurement of Thermal Conductivity by Differential Scanning Calorimetry", pp. 345-350.
Thermochimica Acta, 120 (1987), by J. Bouzon and J. B. Rochette, "Transient Technique for Determining Simultaneously the Thermal Parameters as a Function of Temperature. A Mathematical Treatment", pp. 19-27.
Thermochimica Acta, 34 (1979), by Jen Chiu and P. G. Fair, "Determination of Thermal Conductivity by Differential Scanning Calorimetry", pp. 267-273.
Journal of Applied Polymer Science, vol. 12 (1968), by W. P. Brennan et al., "Thermal Conductivity Measurements with the Differential Scanning Calorimeter", pp. 1800-1802.

*Primary Examiner*—Kevin J. Teska
*Attorney, Agent, or Firm*—Edward Dugas

[57] ABSTRACT

The invention is a method for determining the thermal conductivity of an unknown material using a differential scanning calorimeter. Experiments conducted in a non-adiabatic environment govern the mathematics of the present method. Multiple samples of the unknown material are formed with different lengths and identical cross-sectional areas. Samples of a reference material, having a known thermal conductivity and a density approaching that of the unknown sample, are formed with the same lengths and cross-sectional area as the unknown samples. Each sample is subjected to the same heat rise in a differential scanning calorimeter to determine values of Q heat flow at selected incremental temperatures. A heat equation for the reference sample and the unknown sample is formed and solved for each like length and temperature value of a reference and sample material to determine the thermal conductivity of the unknown sample.

1 Claim, 3 Drawing Sheets

METHOD FOR DETERMINING THERMAL CONDUCTIVITY INCORPORATING DIFFERENTIAL SCANNING CALORIMETRY

TECHNICAL FIELD OF THE INVENTION

The present invention relates to the field of measurement of thermal conductivity, and more particularly to an improved method of measuring thermal conductivity incorporating differential scanning calorimetry.

BACKGROUND OF THE INVENTION

The determination of the thermal conductivity of solid materials is of interest for selecting materials to be used in construction and manufacturing, for example in, processing machinery, and fabrication processes. Of particular interest is the determination of thermal conductivity, generally denoted K, by the use of a heat flow device called a Differential Scanning Calorimeter (DSC). One commercially available type of DSC is supplied by E.I. DuPont de Nemours and Co. under their Model No. 990. Generally speaking, this device utilizes a cylindrical sample of the solid material for test which is placed in a small pan and subjected to a controlled pattern of heat applications while thermocouples record temperatures associated with the sample. One detailed method of analyzing the sample is disclosed in a paper by Jen Chiu and P. G. Fair entitled "Determination of Thermal Conductivity by Differential Scanning Calorimetry", Thermochimica Acta 34 (1979) 267–273. The DSC partially performs the solid state thermal conductivity calculations through the use of a Fourier equation for heat flow (See equation 1).

$$K = \frac{Q \cdot L}{A \cdot (T_2 - T_1)} \quad (1)$$

where; K represents the thermal conductivity, Q is the heat flow, $T_2$ is the temperature of the face of a cylinder of material under test that is heated (i.e., "hot face") and $T_1$ is the temperature of the "cold face", L is the length of the cylinder, and "A" is the cross-sectional area of the cylinder.

The thermal conductivity, K, measurement is made on the cylindrical sample with Q, $T_2$ and $T_1$, stable and the system in "thermal equilibrium". At this point the thermal gradient is firmly established in the material and is not changing.

The advantages of using a DSC approach for K measurement over other heat flow approaches are: 1) the simultaneous acquisition of specific heat data and K data, 2) the option of measuring K while heating the sample at a selected rate, 3) the use of small samples in the DSC, and 4) the short time needed for analysis.

All of the DSC approaches to the measurement of thermal conductivity described in the literature have definite advantages over dedicated thermal conductivity instrumentation but, compromise the utility and strengths of the DSC. The present inventive method of measuring the thermal conductivity value using a DSC as described herein takes full advantage of all that the DSC has to offer to provide K data in a dynamic range (selected rate of change of $T_2$).

SUMMARY OF THE INVENTION

In the method of the present invention various selected lengths of a cylindrical sample of the material to be analyzed are placed in the DSC and a determination of the heat flow Q versus the length L of each sample is made. To determine the K value from the Q versus L values for the unknown material, material of known conductivity is analyzed under identical conditions. Reference samples of the known material having the same cylindrical shape, cross-sectional area, and length, as the sample of the unknown material are run through the DSC so as to generate a set of point values. The point values for like materials of different lengths and like temperatures are grouped together and compared to provide the K values for the unknown material.

A particular advantage of the present method is that the temperature $T_1$ at the one end of the sample, denoted the cold end, need not be measured. In all known techniques where $T_1$ is measured there is a sacrifice in accuracy due to the interface resistance, heat loss, and error in temperature measurement. Additionally, when $T_1$ does not have to be measured the thermal conductivity of powders, liquids and materials as they change phase (e.g. solid to liquid) can be determined.

From the foregoing it can be seen that it is a primary object of the present invention to provide an improved method for determining the thermal conductivity of a material.

Another object of the present invention is to provide a method for determining the thermal conductivity of a material using an equation with one reference temperature being the ambient temperature.

It is a further object of the present invention to provide a method for determining thermal conductivity of a material utilizing a differential scanning calorimeter.

These and other objects of the present invention will become more apparent when taken in conjunction with the following description and drawings wherein like characters indicate like parts and which drawings form a part of the present invention.

DESCRIPTION OF THE PREFERRED EMBODIMENT

Figure 1:
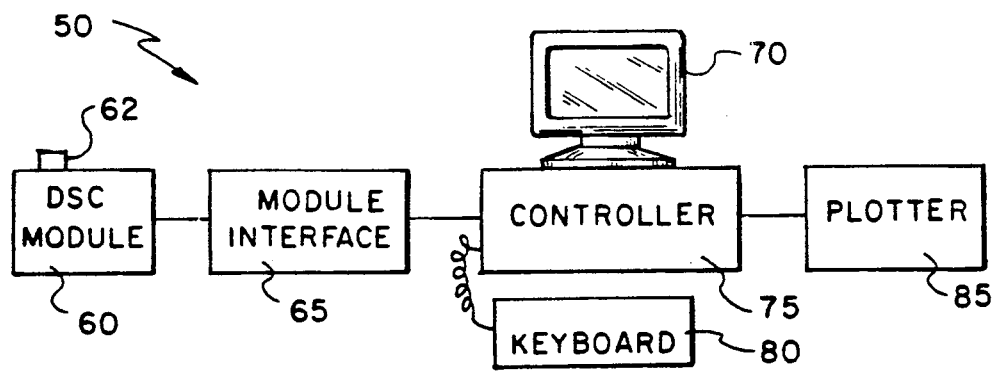
FIG. 1 is a block diagram illustrating one configuration of a commercially available differential scanning calorimeter.

FIG. 1 illustrates in a block diagram form a typical differential scanning calorimeter 50. A DuPont 9900 thermal analyzer was used in the preferred embodiment as the differential scanning calorimeter 50. The calorimeter is comprised of a DSC module 60, having a receptacle 62 for receiving the test samples. The DSC module is interconnected to a module interface 65. The module interface 65 functions to interface a controller 75 to the DSC module 60. A keyboard 80 is coupled to the controller 75 to provide operator input. A color monitor 70 is coupled to the controller 75 for displaying data during the testing of the samples and selection menus for operator interface during set-up. A plotter 85 is utilized for plotting hard copy of the data displayed on the screen 70.

Other types of differential scanning calorimeters may be utilized with the method of the present invention by those persons skilled in the art without undue experimentation.

Figure 2:
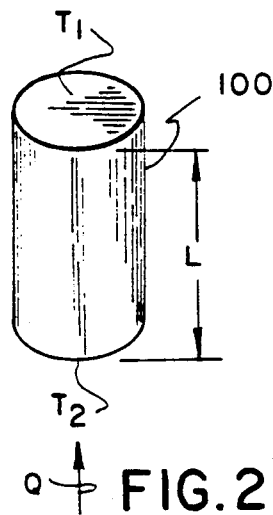
FIG. 2 illustrates one cylindrical sample of length L.

Referring now to FIG. 2, a typical cylindrical sample 100 is shown having a length L, a thermal end, denoted generally as $T_2$, and an opposite thermal end, denoted generally as $T_1$. The direction of heat flow Q is from $T_2$ through the sample to $T_1$. Each of the samples 100 should have an identical cross-sectional area and selected lengths matching the lengths of a reference material. It is not necessary for the samples to have a cylindrical shape; it is only required that the physical geometry of the samples having the same length be the same. As mentioned in the description of FIG. 1, the samples 100 are individually loaded into the receptacle 62 on the DSC module 60 and subjected to testing in accordance with the method of the present invention.

Figure 3:
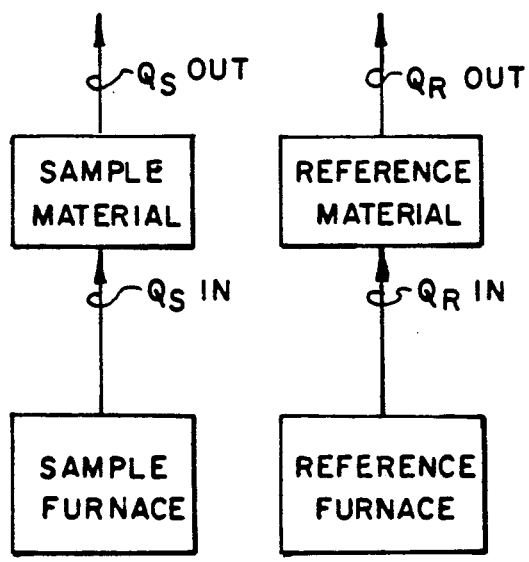
FIG. 3 is a block diagram illustrating the relationship in the DSC between the samples and their associated furnaces for purposes of establishing an understanding of the basic theory of the present method.

Reference is made to FIG. 3 wherein a block diagram simplistically represents a sample material and a reference material positioned over a sample furnace and a reference furnace, respectively. The sample furnace provides a heat flow $q_{Sin}$ to the sample at one end and the sample transmits a heat flow $q_{Sout}$ to the ambient at its other end. In a like manner, the reference furnace provides a heat flow $q_{Rin}$ to the reference material at one end, and the reference transmits a heat flow $q_{Rout}$ to the ambient at its other end.

Figure 4:
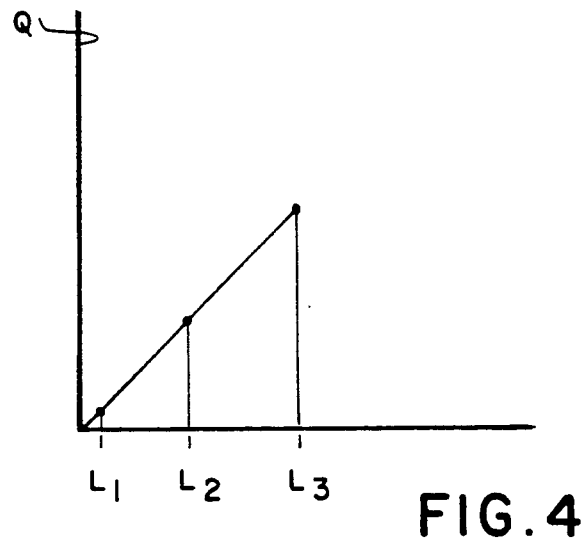
FIG. 4 is a graph illustrating a point plot of Q versus L for three samples of the same material but different lengths.

In FIG. 4 there is shown a Q versus L plot derived at 35° C. for three samples of the same material, each sample having a different length denoted generally as L1, L2, and L3.

Figure 5:
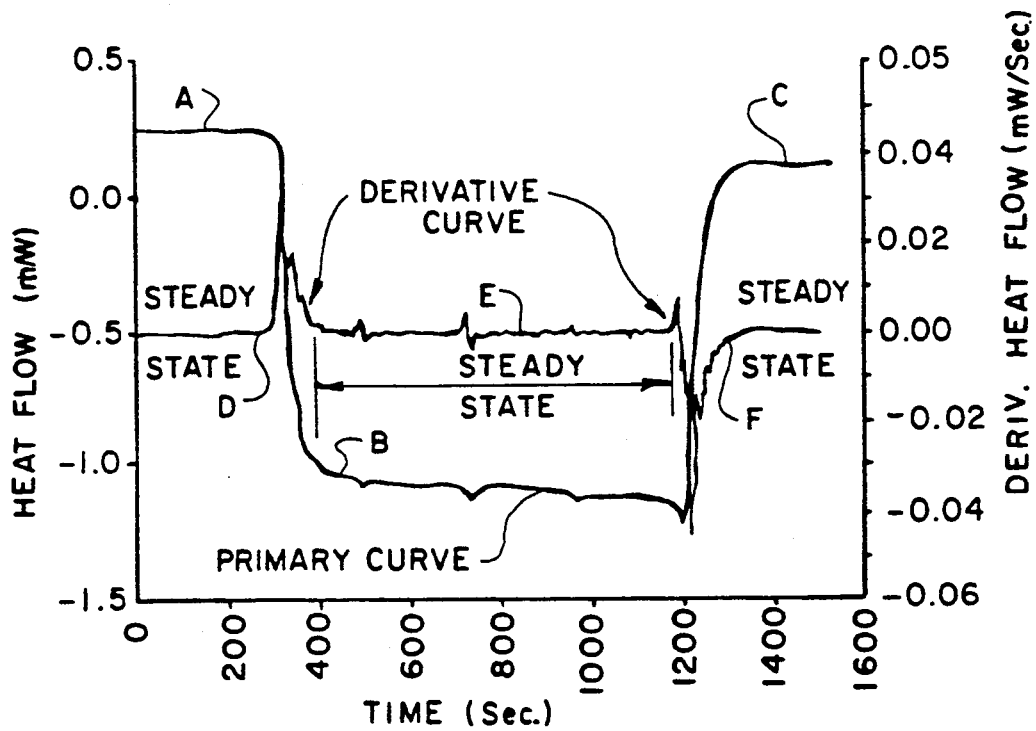
FIG. 5 is a chart illustrating heat flow as a function of time for a tested sample of material.

Referring to the chart of FIG. 5, each sample, whether the reference or an unknown, is subjected to the following temperature cycle in the differential scanning calorimeter:

1) The system is equilibrated at 30° C.
2) Initial temperature is set to 30° C.
3) The sample is held isothermally for 5 minutes. This is shown in the chart as a relatively flat plateau A.
4) The temperature of the sample is ramped at 2° C. per minute up to a temperature of 60° C. This ramping is denoted generally in the primary curve in the area labelled B.
5) The sample is then held isothermally for an additional 5 minutes resulting in the relative flat plateau of the primary curve denoted C. A derivative curve of the primary curve is shown having components D, E, and F. A pseudo-steady state segment of the derivative curve and of the primary curve exists in the areas denoted E, and D, respectively.

In the preferred method of the present invention the number of different lengths selected to provide the output data was three per sample. That is, the reference samples were one, five and ten millimeters long each with a 3.17 millimeter diameter and in a like fashion the unknown samples had the same lengths and the same diameters.

With a 2° C. rise per minute between the 30° C. and 60° C. temperatures and with the computation of the value $K_s$ occurring at each 5° C. increment, seven empirical reference Q versus L curves are generated for the three reference samples and the three unknown samples.

Plots of "Q" versus "L" at 5° C. temperature increments starting at 30° C. and going to 60° C. have been calculated for Styrene, Teflon, Alumina (Coors 96% pure), and Aluminum. For these reference materials, the thermal conductivity is known at every 5° C. from 30° C. to 60° C. A relationship was determined between the slope of the "Q" versus "L" plot (Q/L) and the thermal conductivity. This procedure is carried out at every 5° C. from 30° C. to 60° C. to generate the seven (7) empirical reference curves at 30° C., 35° C., 40° C., 45° C., 50° C., 55° C., and 60° C.

To determine the thermal conductivity of an unknown material, one analyzes the sample under experimental conditions identical to that of one of the four reference materials used above and calculates a (Q/L) value for both the sample and the reference. These values are then compared and normalized to the empirical reference curves calculated at the various temperatures to obtain a value for the thermal conductivity at the temperature of interest.

The thermal conductivity is related to the (Q/L) value using a third order polynomial fit to provide the regression equations set out in the listings appearing in this specification.

In the performance of the method of this invention, testing was performed with the following materials of known thermal conductivity:

| Material | Density (g/cc) | Diameter of Cylinder (cm) | Thermal Conductivity @ 45° C. (W/mK) |
|---|---|---|---|
| Aluminum | 2.65 | 0.317 | 238.000 |
| Teflon | 2.14 | 0.317 | 0.401 |
| Polystyrene | 1.01 | 0.317 | 0.115 |

An empty pan baseline was recorded for each material followed by a DSC scan for each of three lengths of each material. The empty pan refers to the pan used in the thermal analyzer to hold the sample. The following valves for "L" (meters) and "Q" (watts) were taken from the curves generated in the analysis. "Q" is determined through a two point rotation of the sample curve to 0.00 mw at 200 seconds and at 1450 seconds followed by the subtraction of the sample "Q" value at the temperature of interest from the corresponding empty pans baseline "Q" value. The "L" value is calculated using the relationship:

$$L = \frac{\text{mass}}{(\text{Density})(\text{Area})} = \frac{g}{(g/cm^3)(cm^2)}$$

The density of the material is determined from the larger "L" samples, the cross-sectional area is measured and the sample is weighed to obtain the mass.

Examination of the data indicates that it is necessary to evaluate only the 1, 3 and 5 mm lengths of each material to calculate the slope (Q/L) of the Q versus L plot:

| L (measured) | Mass | L (calculated) | Q (Watts) |
|---|---|---|---|
| For Aluminum: @45° C., Density = 2.65 g/cm$^3$, D = 0.3175 cm | | | |
| $0.9906 \times 10^{-3}$m | 20.34 mg | $0.9695 \times 10^{-3}$m | $0.5805 \times 10^{-3}$ |
| $2.9718 \times 10^{-3}$m | 62.24 mg | $2.9665 \times 10^{-3}$m | $1.7533 \times 10^{-3}$ |
| $4.9022 \times 10^{-3}$m | 104.21 mg | $4.9669 \times 10^{-3}$m | $2.8603 \times 10^{-3}$ |
| (Q/L) = 0.5703  r$^2$ = 0.9997 | | | |
| For Teflon: @45° C., Density = 2.14 g/cm$^3$, D = 0.3175 cm | | | |
| $1.0414 \times 10^{-3}$m | 16.63 mg | $0.982 \times 10^{-3}$m | $0.5401 \times 10^{-3}$ |
| $3.1242 \times 10^{-3}$m | 52.52 mg | $3.100 \times 10^{-3}$m | $1.3670 \times 10^{-3}$ |
| $5.1303 \times 10^{-3}$m | 86.13 mg. | $5.084 \times 10^{-3}$m | $1.8020 \times 10^{-3}$ |
| (Q/L) = 0.3086  r$^2$ = 0.9751 | | | |
| For Polystyrene: @45° C., Density = 1.01 g/cm$^3$, D = 0.3175 cm | | | |
| $1.0922 \times 10^{-3}$m | 9.14 mg | $1.143 \times 10^{-3}$m | $0.4095 \times 10^{-3}$ |
| $2.8894 \times 10^{-3}$m | 24.07 mg | $3.010 \times 10^{-3}$m | $0.8579 \times 10^{-3}$ |
| $4.8514 \times 10^{-3}$m | 40.49 mg. | $5.063 \times 10^{-3}$m | $1.1402 \times 10^{-3}$ |
| (Q/L) = 0.1856  r$^2$ = 0.9753 | | | |

As previously stated, the thermal conductivity is related to the (Q/L) value using a third order polynomial fit to provide the regression equations shown below. This procedure is carried out at every 5° C. from 30° C. to 60° C. to generate the seven (7) empirical reference curves at 30° C., 35° C., 40° C., 45° C., 50° C. 55° C. and 60° C.

These equations contain a fourth data point of an alumina sample which was tested as an unknown against the three known materials. It was included in the plot to better define the curve.

| ROW | X | Y | X2 | X3 |
|---|---|---|---|---|
| 1 | 0.1846 | 0.114 | 0.034077 | 0.006291 |
| 2 | 0.3107 | 0.405 | 0.096534 | 0.029993 |
| 3 | 0.4230 | 24.500 | 0.178929 | 0.075687 |
| 4 | 0.5785 | 237.174 | 0.334662 | 0.193602 | regress C2 on 3 C1 C3 C4, NOTE
X is highly correlated with other predictor variables
X2 is highly correlated with other predictor variables
X3 is highly correlated with other predictor variables.

The regression equation is $$Y = -160 + 1875X - 7072X2 + 8671X3$$

| Predictor | Coef | Stdev | t-ratio |
|---|---|---|---|
| Constant | −159.618 | 0.00000 | . |
| X | 1875.36 | 0.0000 | . |
| X2 | 7072.34 | 0.000 | . |
| X3 | 8671.11 | 0.000 | . |

At 45° C.

| ROW | X | Y | X2 | X3 |
|---|---|---|---|---|
| 1 | 0.1856 | 0.115 | 0.034447 | 0.006393 |
| 2 | 0.3086 | 0.408 | 0.095234 | 0.029389 |
| 3 | 0.4223 | 23.999 | 0.178337 | 0.075312 |
| 4 | 0.5703 | 236.859 | 0.325242 | 0.185485 | regress C2 on 3 C1 C3 C4. NOTE
X is highly correlated with other predictor variables
X2 is highly correlated with other predictor variables
X3 is highly correlated with other predictor variables.

The regression equation is $$Y = -192 + 2227X - 8273X2 + 9973$$

| Predictor | Coef | Stdev | t-ratio |
|---|---|---|---|
| Constant | −191.909 | 0.00000 | . |
| X | 2226.61 | 0.0000 | . |
| X2 | 8273.32 | 0.000 | . |
| X3 | 9972.54 | 0.000 | . |

At 50° C.

| ROW | X | Y | X2 | X3 |
|---|---|---|---|---|
| 1 | 0.1873 | 0.116 | 0.035081 | 0.006571 |
| 2 | 0.3094 | 0.410 | 0.095728 | 0.029618 |
| 3 | 0.4341 | 23.750 | 0.188443 | 0.081803 |
| 4 | 0.5805 | 236.559 | 0.336980 | 0.195617 | regress C2 on 3 C1 C3 C4. NOTE
X is highly correlated with other predictor variables
X2 is highly correlated with other predictor variables
X3 is highly correlated with other predictor variables, The regression equation is $$Y = -208 + 2360X - 8537X2 + 9977X3$$

| Predictor | Coef | Stdev | t-ratio |
|---|---|---|---|
| Constant | −207.926 | 0.00000 | . |
| X | 2359.84 | 0.0000 | . |
| X2 | 8537.62 | 0.000 | . |
| X3 | 9976.66 | 0.000 | . |

At 55° C.

| ROW | X | Y | X2 | X3 |
|---|---|---|---|---|
| 1 | 0.1905 | 0.117 | 0.036290 | 0.006913 |
| 2 | 0.3032 | 0.412 | 0.091930 | 0.027873 |
| 3 | 0.4326 | 23.400 | 0.187316 | 0.081070 |
| 4 | 0.5802 | 236.260 | 0.336632 | 0.195314 | regress C2 on 3 C1 C3 C4. NOTE
X is highly correlated with other predictor variables
X2 is highly correlated with other predictor variables
X3 is highly correlated with other predictor variables.

The regression equation is $$Y = -206 + 2329X - 8436X2 + 9884X3$$

| Predictor | Coef | Stdev | t-ratio |
|---|---|---|---|
| Constant | 205.798 | 0.00000 | . |
| X | 2329.30 | 0.0000 | . |
| X2 | −8436.02 | 0.000 | . |
| X3 | 9883.76 | 0.000 | . |

At 60°

| ROW | X | Y | X2 | X3 |
|---|---|---|---|---|
| 1 | 0.1907 | 0.119 | 0.036366 | 0.006935 |
| 2 | 0.3059 | 0.415 | 0.093575 | 0.028625 |
| 3 | 0.4415 | 23.000 | 0.194922 | 0.086058 |

-continued

| ROW | X | Y | X2 | X3 |
|---|---|---|---|---|
| 4 | 0.5863 | 235.950 | 0.343748 | 0.201539 | regress C2 on 3 C1 C3 C4. NOTE
X is highly correlated with other predictor variables
X2 is highly correlated with other predictor variables
X3 is highly correlated with other predictor variables.
The regression equation is $$Y = -222 + 2482X - 8824X2 + 10104X3$$

| Predictor | Coef | Stdev | t-ratio |
|---|---|---|---|
| Constant | −222.443 | 0.00000 | . |
| X | 2428.44 | 0.0000 | . |
| X2 | −8824.26 | 0.000 | . |
| X3 | 10103.5 | 0.000 | . |

Alumina (96° pure Coors) was analyzed using aluminum as the reference material. It was discovered that in order for the method to work accurately the (lengths) of the alumina needed to be adjusted to the density of the aluminum reference. The unknown material density must be within the range of the reference material's density otherwise the lengths of the unknown material will have to be adjusted to match the density of the reference material being used.

Alumina

| L | (0.1038) Q40 | (0.1049) Q45 | (0.1060) Q50 | (0.1051) Q55 | (0.1028) Q60 |
|---|---|---|---|---|---|
| $1.804 \times 10^{-3}$ | 0.9829 | 0.9962 | 1.0165 | 1.0318 | 1.0325 |
| $4.500 \times 10^{-3}$ | 2.2908 | 2.3209 | 2.3450 | 2.3881 | 2.3908 |
| $7.268 \times 10^{-3}$ | 3.3988 | 3.4129 | 3.4560 | 3.5111 | 3.5308 |
| $10.009 \times 10^{-3}$ | 4.2658 | 4.2949 | 4.3610 | 4.4151 | 4.4538 |
| $13.612 \times 10^{-3}$ | 4.9718 | 5.0489 | 5.1120 | 5.1731 | 5.2148 |

Alumina stack Q/L in W/m: 0.3384, 0.3429, 0.3472, 0.3507, 0.3547 compared to aluminum.

Alumina Q/L in W/m values normalized to aluminum solid cylinder: 0.4230, 0.4223, 0.4341, 0.4328, 0.4415.

The alumina unknown was supplied in wafer form. Analysis was carried out through the stacking of 3 mm diameter disks to achieve the desired lengths. The aluminum reference was analyzed in like fashion and then normalized to the previously analyzed solid cylinder Q/L data.

Aluminum

| L | (0.1038) Q40 | (0.1049) Q45 | (0.1060) Q50 | (0.1051) Q55 | (0.1028) Q60 |
|---|---|---|---|---|---|
| $1.2385 \times 10^{-3}$ | 0.7714 | 0.7741 | 0.7890 | 0.7891 | 0.7875 |
| $3.0999 \times 10^{-3}$ | 1.8268 | 1.8419 | 1.8600 | 1.8591 | 1.8668 |
| $4.9671 \times 10^{-3}$ | 2.7408 | 2.7409 | 2.7790 | 2.7851 | 2.7798 |
| $6.9407 \times 10^{-3}$ | 3.5848 | 3.5879 | 3.5970 | 3.6271 | 3.6258 |
| $9.4100 \times 10^{-3}$ | 4.5808 | 4.5919 | 4.6230 | 4.6661 | 4.6768 |

Q/L value in W/m for stacked disks of aluminum to achieve desired L: Stack: 0.4628, 0.4631, 0.4643, 0.4701, 0.4710.

Q/L value in W/m for solid cylinder of aluminum of desired L: Cylinder: 0.5785, 0.5703, 0.5805, 0.4802, 0.5863.

For Alumina

| Temperature °C. | For Alumina K Experiment | K Literature |
|---|---|---|
| 20 | — | 26.0 |
| 30 | — | — |
| 40 | 25.2 | — |
| 50 | 24.8 | — |
| 60 | 24.0 | — |
| 70 | — | — |
| 80 | — | — |
| 90 | — | — |
| 100 | — | 20.0 |

Figure 7:
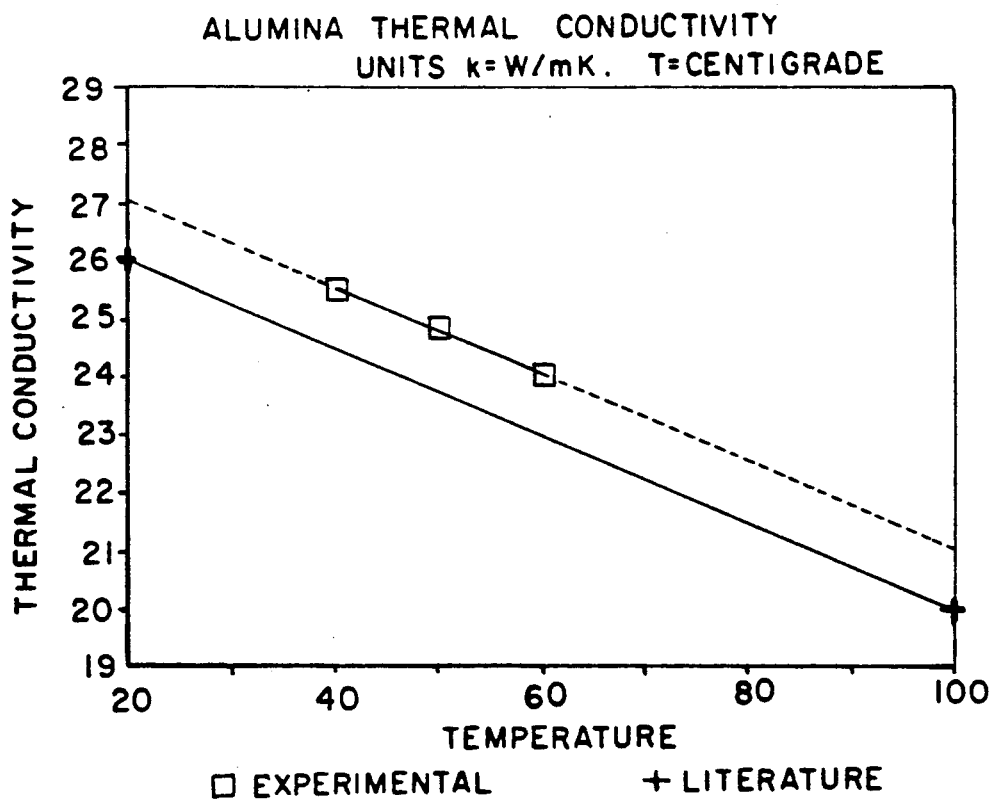
FIG. 7 is a plot of the thermal conductivity of a known material and the plot of the thermal conductivity of an unknown material determined by the method of the present invention.
Figure 6:
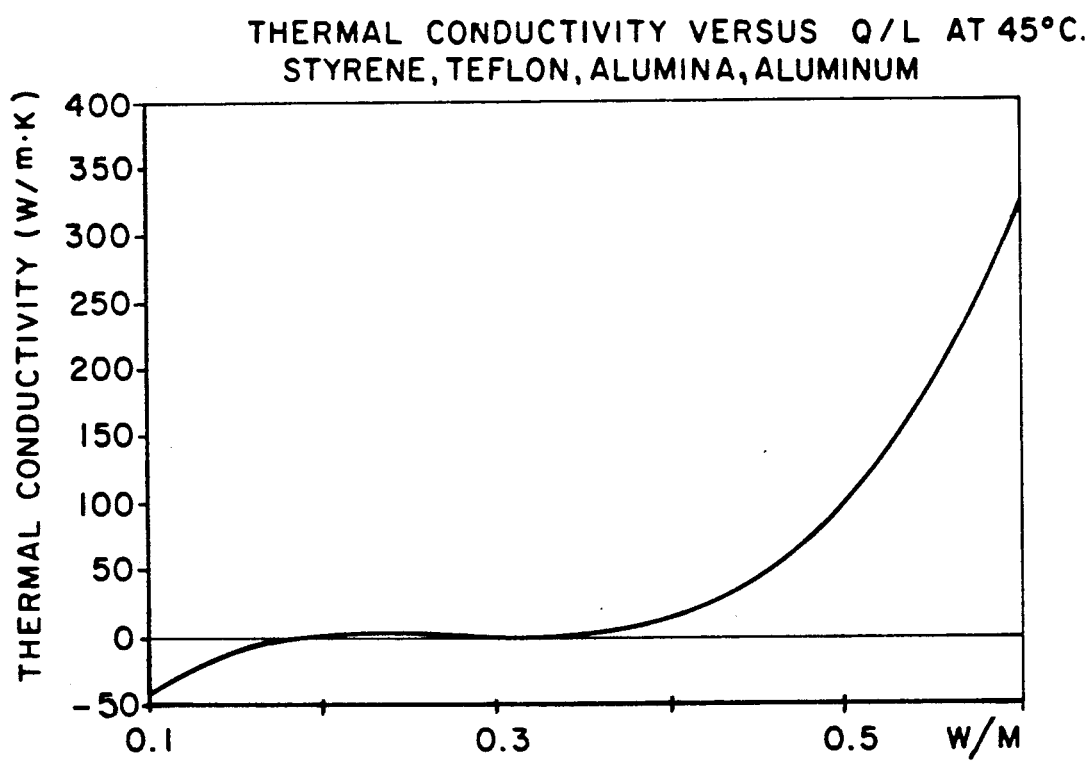
FIG. 6 illustrates an empirical plot fit with a third order polynomial at 45° C. of thermal conductivity vs Q/L for four types of materials.

FIG. 7 illustrates the plot of the above values.

From the foregoing it can be seen that to determine the thermal conductivity of an unknown material, one simply analyzes the unknown under experimental conditions identical to that of one of the four reference materials used above and calculates a (Q/L) value for both the unknown and the reference at a plurality of different temperatures. These values are then compared to the empirical reference curve calculated at the selected temperature to obtain a value of thermal conductivity at that temperature. Appendix A (available in the application file) is a program written in IBM 3.0 Basic for performing the method of the present invention on a DuPont 9900 DSC.

While there has been shown what is considered to be the preferred embodiment of the present invention, it will be manifest that many changes and modifications may be made therein without departing from the essential spirit of the invention. It is intended, therefore, in the annexed claims, to cover all such changes and modifications as may fall within the true scope of the invention.

I claim:

1. A method for determining the thermal conductivity K of a material of unknown thermal conductivity utilizing a differential scanning calorimeter comprising the steps of:
   (a) forming cylindrical samples of equal diameters and of different lengths L of reference materials having known thermal conductivity K values;
   (b) forming cylindrical samples having lengths L and diameters corresponding to the samples of step (a) of a material of unknown thermal conductivity K;
   (c) subjecting each sample to the following steps in a differential scanning calorimeter:
      1. Equilibrate each sample and said scanning calorimeter at 30.00° C.
      2. Initialize the temperature of said scanning calorimeter to 30.00° C.

3. Hold the sample isothermally for 5 min.
4. Ramp the temperature of said scanning calorimeter at 2.00° C./min to 60.00° C.
5. Measure the temperature of each sample, at the end contacting said scanning calorimeter, at each 5° C. rise in said scanning calorimeter between 30.00° C. and 60.00° C.;
6. Hold the sample isothermally for 5 min;

(d) forming a Q divided by L value for each sample at each 5° C. interval between 30° C. and 60° C. wherein Q is the value of heat flow through a sample;

(e) forming a Q divided by L library of values for each reference sample and for each sample of unknown material of different length L at the same temperatures;

(f) forming a thermal conductivity versus Q divided by L computation for each reference sample and for each sample of unknown material of different length at the same temperature utilizing the library of values of step (e); and (g) comparing the computations of step (f) associated with a sample of unknown material against the computations of a reference sample of known K to determine the thermal conductivity K of the sample of unknown material.

* * * * *